(12) United States Patent
Cao et al.

(10) Patent No.: US 8,889,429 B2
(45) Date of Patent: Nov. 18, 2014

(54) WATER-SOLUBLE NANOCRYSTALS THROUGH DUAL-INTERACTION LIGANDS

(75) Inventors: Y. Charles Cao, Gainesville, FL (US); Huimeng Wu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 921 days.

(21) Appl. No.: 12/865,056

(22) PCT Filed: Jan. 28, 2009

(86) PCT No.: PCT/US2009/032212
§ 371 (c)(1),
(2), (4) Date: Aug. 17, 2010

(87) PCT Pub. No.: WO2009/097319
PCT Pub. Date: Aug. 6, 2009

(65) Prior Publication Data
US 2010/0311080 A1    Dec. 9, 2010

Related U.S. Application Data

(60) Provisional application No. 61/062,750, filed on Jan. 28, 2008.

(51) Int. Cl.
*G01N 33/553* (2006.01)
*G01N 33/543* (2006.01)
*C01B 19/00* (2006.01)

(52) U.S. Cl.
CPC .... *G01N 33/54353* (2013.01); *G01N 33/54313* (2013.01); *C01B 19/007* (2013.01)
USPC .......................................... 436/525; 436/518

(58) Field of Classification Search
CPC .................. G01N 33/54326; G01N 33/54346; G01N 33/6803; G01N 33/54313; G01N 33/54353; C23C 18/1216
USPC .................................................. 436/518, 525
See application file for complete search history.

(56) References Cited

U.S. PATENT DOCUMENTS

| 7,153,703 B2 | 12/2006 | Peng et al. |
| 2001/0040232 A1 | 11/2001 | Bawendi et al. |
| 2004/0022938 A1 * | 2/2004 | Kato et al. .................... 427/212 |

OTHER PUBLICATIONS

Smith et al. Phys. Chem. Chem. Phys. 2006, 8, 3895.* Dubertret et al. Science 2002, 298, 1759-1763.*
Doty et al. Chem. Mater. 2005, 17, 4630.*

(Continued)

*Primary Examiner* — Bao Thuy L Nguyen
*Assistant Examiner* — Pensee Do
(74) *Attorney, Agent, or Firm* — Saliwanchik, Lloyd & Eisenschenk

(57) ABSTRACT

A dual-interaction ligand for rendering otherwise hydrophobic nanoparticles water soluble or suspendable has a hydrophilic base with a plurality of hydrophilic segments extending from a core of the base, where at least one segment or the core contains a hydrophobic groups capable of forming van der Waal interaction between hydrophobic groups of the dual-interaction ligand and other hydrophobic ligands, and at least one complexing functionality to complex a metal atom or ion of a nanoparticle. The dual-interaction ligands can be combined with hydrophobic nanoparticles, where the dual-interaction ligands can displace some or all of the hydrophobic ligands of the hydrophobic nanoparticles, to form a nanoparticle-dual interaction ligand complex that can be dissolved or dispersed readily in an aqueous solution. The dual interaction ligand can be functionalized to attach an antibody or other biomolecules such that the nanoparticle dual-interaction ligands complexes can contain biomolecules. Such biomolecules modified nanoparticle dual-interaction ligands can be used for sensing, labeling, optical imaging, magnetic resonance imaging, cell separation, and treatment of diseases.

30 Claims, 9 Drawing Sheets

(56) References Cited

OTHER PUBLICATIONS

Hong, R. et al., "Surface PEGylation and Ligand Exchange Chemistry of FePt Nanoparticles for Biological Applications," *Chem. Mater.*, 2005, pp. 4617-4621, vol. 17.

Yu, W.W. et. al., "Forming Biocompatible and Nonaggregated Nanocrystals in Water Using Amphiphilic Polymers," *J. Am. Chem. Soc.*, 2007, pp. 2871-2879, vol. 129, No. 10.

* cited by examiner w+x+y+z=20
n = 1 to 30
n' = 1 to 40
R=$C_6H_{13}$ to $C_{30}H_{61}$
R'= functional group:

R"= -$\overset{\oplus}{N}(CH_3)_3$, or -$\overset{\ominus}{COO}$

WATER-SOLUBLE NANOCRYSTALS THROUGH DUAL-INTERACTION LIGANDS

CROSS-REFERENCE TO RELATED APPLICATION

This application is the U.S. national stage application of International Patent Application No. PCT/US2009/032212, filed on Jan. 28, 2009, which claims the benefit of U.S. Provisional Application Ser. No. 61/062,750, filed Jan. 28, 2008, the disclosures of which are hereby incorporated by reference herein in, their entireties, including any figures, tables, or drawings.

GOVERNMENT SUPPORT

The subject matter of this application has been supported by a research grant from the National Science Foundation under grant number DMR-0645520 and a research grant from the Department of the Navy, Office of Naval Research under grant number N00014-06-1-0911. Accordingly, the government has certain rights in this invention.

BACKGROUND OF THE INVENTION

Because of their unique size-dependent optical, electronic, magnetic, and chemical properties, inorganic nanocrystals are becoming a new class of powerful tools in biological and medical applications for sensing, labeling, optical imaging, magnetic resonance imaging, cell separation, and treatment of disease. These applications require nanocrystals that are soluble and stable in aqueous solutions. To achieve water soluble and stable nanocrystals, nanocrystal coatings are needed because high-quality nanocrystals are generally synthesized in organic solutions and stabilized by hydrophobic ligands.

Presently, two general approaches have been developed for the coatings of hydrophobic nanocrystals with organic ligands to render them hydrophilic. The first approach is based on coordinate bonding. Functional groups (such as thiol, dithiol, phosphine and dopamine) are used to directly link hydrophilic groups onto the surface of hydrophobic nanocrystals, and displacing the hydrophobic ligands. The second approach uses hydrophobic van der Waals interactions between the hydrophobic ligands of the nanocrystals as prepared and hydrophobic tails of amphiphilic ligands, where the hydrophobic ligands on the nanocrystals are not displaced, and forming nanocrystal-micelles.

Unfortunately, water-soluble nanocrystals made by these two approaches often suffer from low stability and/or display high non-specific binding with non-target biomolecules. Water-soluble nanocrystals coated with PEGylated amphiphilic polymers have been shown to have very high stability and low nonspecific-absorption levels. Unfortunately, PEGylated polymer shells typically suffer from large hydrodynamic diameters (HDs) on the order of 30-40 nm, which can limit their use in applications such as in vivo cell imaging.

Therefore, the goal remains to develop stable water soluble nanocrystals which do not suffer from non-specific binding and have small hydrodynamic diameters. It also remains a goal to form water soluble nanocrystals that can be bound to an antibody or other biomolecules to allow specific interactions with specific biomolecules.

BRIEF SUMMARY OF THE INVENTION

A dual-interaction ligand for rendering nanoparticles water soluble combines a hydrophilic base with a plurality of segments extending from a core of the hydrophilic base, where at least one segment or the core is connected to a metal coordinating functionality and at least one segment or the core is connected to a hydrophobic functionality. The metal coordinating functionalities and the hydrophobic functionalities are generally attached by linking groups to the hydrophilic base.

In one embodiment of the invention, the hydrophobic base with the hydrophilic functionality is derived from polyethylene glycol (PEG) sorbitan fatty-acid esters which are available and known as Tween® molecules such as Tween®-20, Tween®-40, Tween®-60, and Tween®-80. The Tween molecule can be derivatized to contain a metal coordinating functionality. The metal coordinating functionality can be a bidentate such as a dithiol or a diol.

The dual-interaction ligand can be combined with hydrophobic nanoparticles to form nanoparticle-dual-interaction ligand complexes that are water soluble or suspendable. The hydrophobic nanoparticles can be metal, metal oxide, or semiconductor nanocrystals which are hydrophobic due to the hydrophobic ligands that are used to form and stabilize the nanoparticles. By displacing some or all of the hydrophobic ligands with the dual-interaction ligands, a very stable hydrophilic nanoparticle is formed.

The dual-interaction ligand can also contain functionality such that an antibody or other biomolecules can be attached to the dual-interaction ligand ultimately to a nanoparticle. These nanoparticle-dual-interaction ligand complexes that are further modified with antibodies can be used in a variety of applications including, for example, sensing, labeling, optical imaging, magnetic resonance imaging, cell separation, and treatment of diseases.

DETAILED DESCRIPTION OF THE INVENTION

Embodiments of the invention are directed to a new class of ligands to produce water-soluble nanocrystals. The ligands are dual-interaction ligands where binding to the surface of hydrophobic nanocrystal occurs through coordinate bonding and simultaneously through hydrophobic van der Waals interactions. The resulting nanocrystals are water-soluble and have relatively small HDs, of less than 20 nm. The nanocrystals having dual-interacting ligands exhibit extraordinary stability in a wide range of pH, salt concentration, and temperature. The nanocrystals having dual-interacting ligands can be further functionalized with antibodies and used, for example, for monitoring virus-protein expression in cells. Various dual-interacting ligands of the present invention allow the formation of water-soluble nanocrystals of various types, for example, of gold, $Fe_3O_4$ and CdSc/ZnS quantum dots (QDs). The nanocrystals can comprise metal such as Au, Ag, Ag/Au, Co, Pt, Pd, Cu, or any combination thereof. The nanocrystal can comprise a metal oxide such as $Fe_3O_4$, $Fe_2O_3$, $In_2O_3$, ZnO, $TiO_2$, $Gd_2O_3$, or any combination thereof. The nanocrystals can comprise a semiconductor, such as CdSe/ZnS, CdS/ZnS, CdS, CdSe, CdTe, InAs, InP, InP/ZnS, InAs/ZnSe, PbSe, PbS, PbTe, or any combination thereof.

Figure 1:
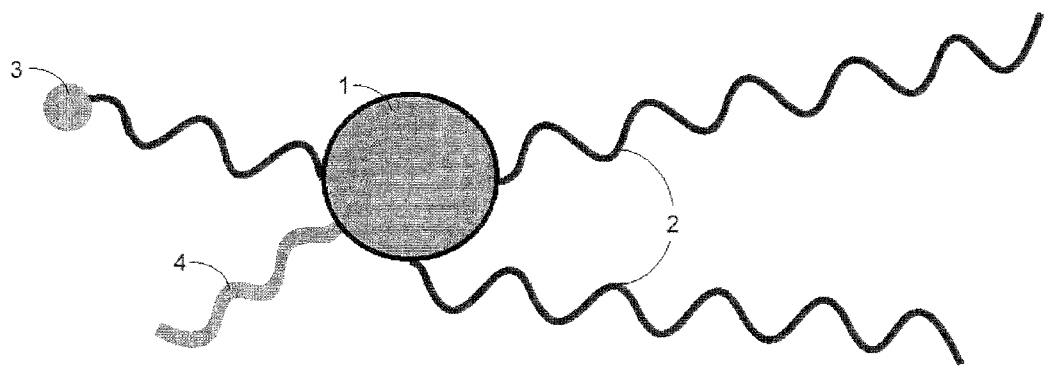
FIG. 1 shows a generalized dual-inaction ligand according to embodiments of the invention.
Figure 2:
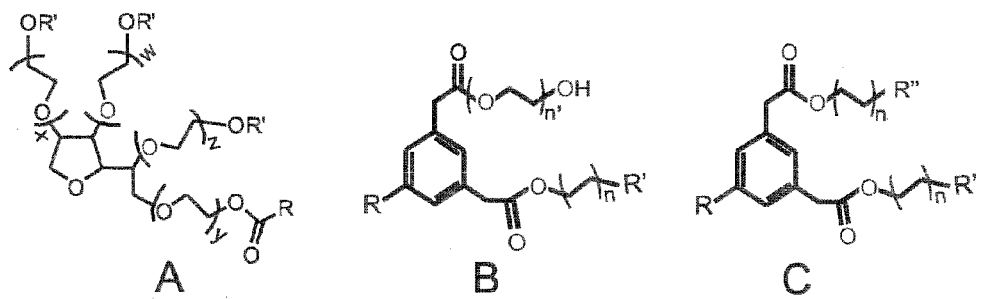
FIG. 2 shows three different types of dual-inaction ligands that differ by at least one of the type of core, metal coordinating functionality, hydrophobic functionality, and portions of a hydrophilic base extending from the core according to embodiments of the invention.
Figure 2:
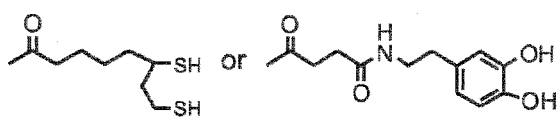

A dual-interaction ligand according to embodiments of the invention are shown in FIG. 1 where the dual-interaction ligand comprises a core 1 of a hydrophilic base with a plurality of hydrophilic segments 2 extending from the core 1; at least one segment or the core containing a metal coordinating functionality 3; and at least one segment or the core containing or being a hydrophobic functionality 4. The metal coordinating functionalities 3 and the hydrophobic functionalities 4 are generally attached to the segments by linking groups which can be the same or different. FIG. 2 shows three different types of dual-interaction ligands where the core is either a sugar residue A), or an aromatic hydrocarbon B) and C), with one or more polyether hydrophilic segments A) and B), or ionic groups C), a C4 to C30 hydrocarbon chain as a hydrophobic group, and a functional group for coordination to a metal. The functionality for coordination to the metal can be attached through a linking group to any of the hydrophilic segments, hydrophobic segments or the core of the hydrophilic base. According to other embodiments of the invention, other cores, hydrophilic groups, hydrophobic groups and metal coordinating groups can be used as can be appreciated by one skilled in the art.

The dual-interaction ligands are constructed from a hydrophilic base with multiple portions of the hydrophilic base extending from a core. For example, the multiple segments can be multiple linear arms extending from a core or the multiple segments can be multiple loops or dendritic branches extending from a core. The core can be a single polyvalent atom, such as a carbon or silicon atom, a cyclic fragment with multiple sights for attachment of the multiple segments, such as a sugar residue, a multifunctional cycloalkane, aromatic hydrocarbon, or cyclosiloxane, a branched hydrocarbon with multiple functional groups on the branches, or any combination of the these types of structures.

The dual-interaction ligands have at least one interaction site resulting from a hydrophobic functionality. The hydrophobic functionality is generally a C4 to C30 chain where the C4 to C30 chain can form a hydrophobic or van der Waal interaction with another C4 to C30 chain. The hydrophobic functionality can be of a single functionality, for example where all molecules are one of C8, C18 or any other length carbon chain, or a mixture of hydrophobic functionality, for example a distribution of carbon chain lengths that average to be C8, C18 or any other length carbon chain. Other hydrophobic functionality can be used as long as a sufficiently strong interaction can be formed. The hydrophobic group can be coupled to a segment as any functionality, including an ester, thioester, amide, imide, ether, amine, alkenyl, alkynyl, or other linking group where the linking group is sufficiently hydrolytically stable under the conditions of intended use of the dual-interacting ligand.

The dual-interaction ligands have at least one interaction site resulting from complexing functionality. The functionality can have the capacity to act as a monodentate, bidentate, or polydentate. As the complexing functionality is generally required to displace a ligand that is attached to a hydrophobic nanoparticle, a bidentate of polydentate is particularly useful to drive the equilibrium toward complexation of a dual-interaction ligand. The complexing functionality can be an group capable of complexing to a metal atom or ion and, for example, can be a thiol, hydroxy, amine or phosphine group or a combination of two or more of these groups, generally positioned in a relatively close proximity to each other, for example, being separated by 3 or 4 covalent bonds. The complexing functionality can be attached via a linking group, such as described above for the attachment of a hydrophobic group to a segment.

Generally, the nanoparticle, to which the dual-interaction ligand is ultimately attached, is prepared in a non-aqueous system. The nanoparticle is a metal, metal oxide or semiconducting nanocrystal or nanoparticle and is formed and stabilized using hydrophobic ligands. The dual-interaction ligand displaces some or all of these hydrophobic ligands to form a nanoparticle-dual-interaction ligand complex that can, and generally does, include undisplaced hydrophobic ligands. The hydrophobic interaction is formed between two dual-interaction ligands, or between one dual-interaction ligand and a hydrophobic ligand.

In one embodiment of the invention, the dual-interaction ligands provide a bidentate group for coordinate bonding and a hydrophobic chain of sufficient size to interact with one or more hydrophobic chains that are present from the preparation of the nanoparticle's core. In an embodiment of the invention, the dual-interaction ligand is derived from a polyoxyethylenesorbitan mono ester of a fatty acid by the addition of a single bidentate group for coordination to a nanoparticle surface. In one embodiment of the invention the bidentate group is a dithiol group where the second thiol group is situated on an adjacent carbon to that containing the first thiol group or is situated on a carbon separated by no more that two bonds from the carbon containing the first thiol group. Such dithiol functionalized dual-interaction ligands are appropriate for solublizing metal and metal alloy nanoparticles in aqueous solution. In another embodiment, the bidentate group is a diol, again where the hydroxyl groups are situated on adjacent carbons or carbons that are separated by no more than two bonds. Such diol functionalized dual-interaction ligands are appropriate for solubilizing metal oxide nanoparticles in aqueous solution.

Figure 3:
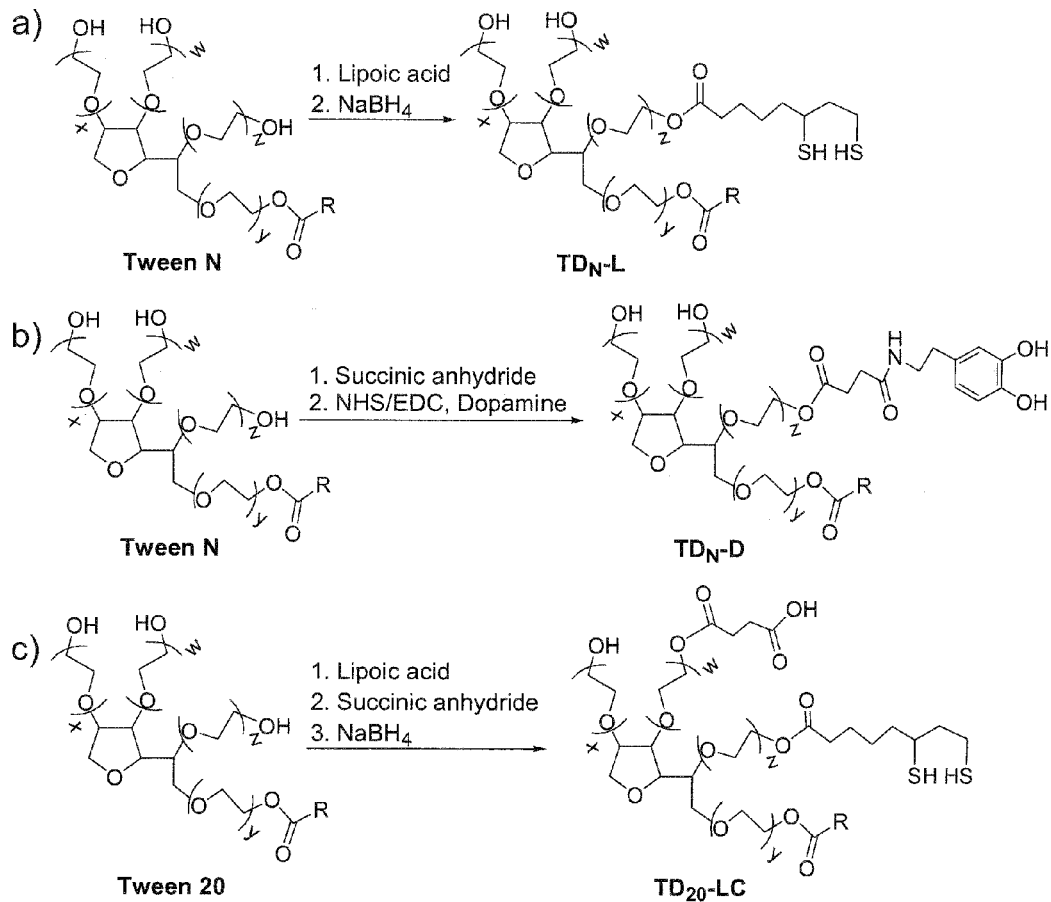
FIG. 3 shows chemical structures and equations for the transformation of polyethylene glycol (PEG) sorbitan fatty-acid esters to dual-interaction ligands with a) a dithiol coordinating group, b) a diol coordinating group, and c) a dithiol coordinating group and a carboxyl group.
Figure 4:
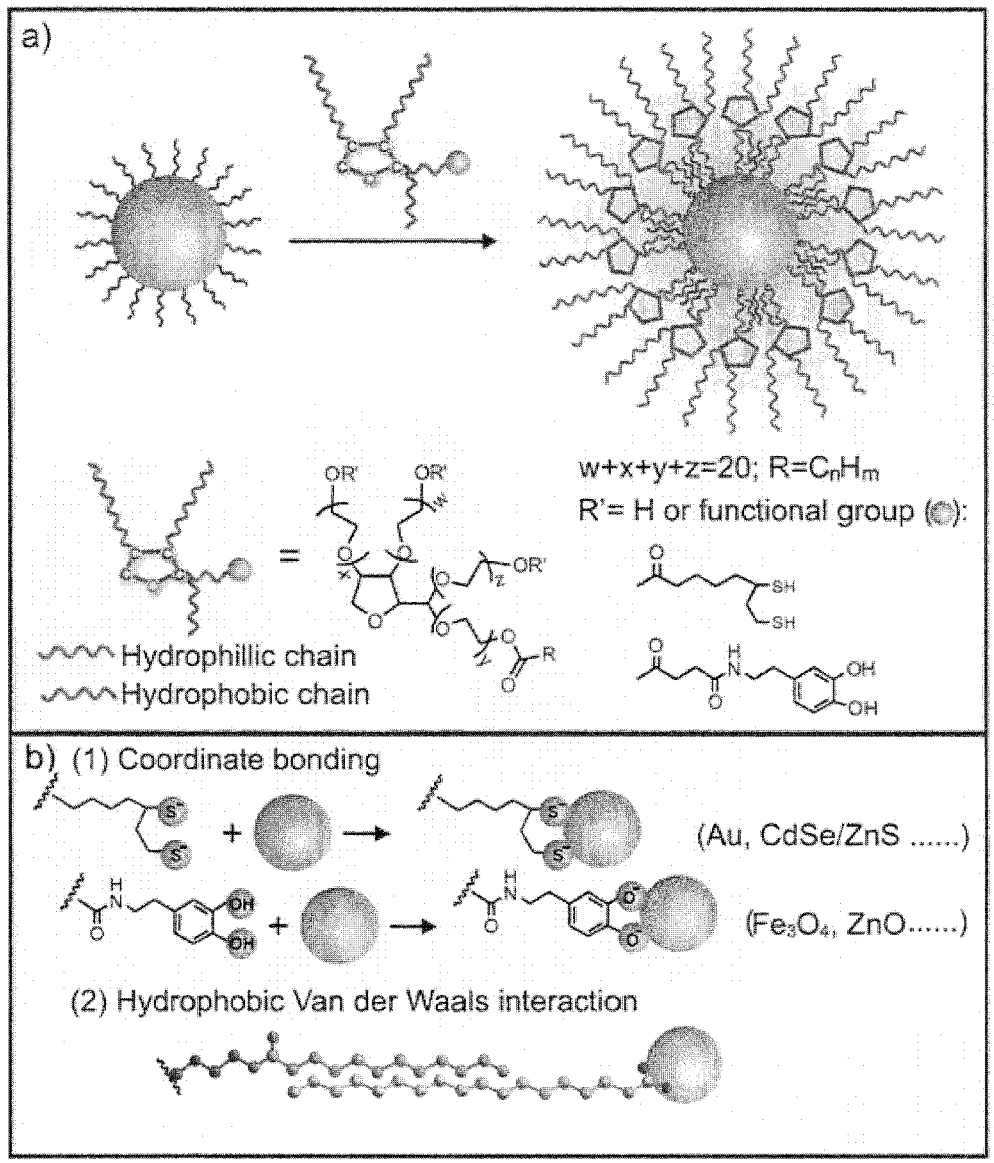
FIG. 4 is a) a schematic illustration of the formation of a dual-interaction ligand nanoparticle from a hydrophobic nanoparticle and dual-interaction ligands and the structure of the dual action ligands according to an embodiment of the invention, and b) a schematic illustration of the two modes of interaction between a dual-interaction ligand and a nanoparticle.

In one embodiment of the invention the dual-interaction ligands are modified polyethylene glycol (PEG) sorbitan fatty-acid esters derived from Tween® 20, Tween®40, Tween® 60 and Tween® 80, where Tween® is a registered trademark of ICI Americas, Inc. These PEG sorbitan fatty-acid esters have 20 ethylene-glycol units distributed among their four branches, or segments, and the number indicates the type of their fatty-acid tail as indicated in FIG. 3. The general structure and mode of interactions with a nanoparticle is shown in FIG. 4. Because of their relative nontoxicity, Tween® compounds are often used in the food industry (as food additives). More importantly, Tween® compounds are widely used as protein stabilizing and blocking agents to minimize non-specific binding in immunoassays such as western blotting and ELISA (enzyme-linked immunosorbent assay). These properties make Tween® compounds attractive for coating water-soluble nanocrystals for use in biomedical applications. However, Tween® compounds cannot be directly used to stabilize hydrophobic nanocrystals in water because the hydrophobic van der Waals interactions of their fatty-acid tails and hydrophobic nanocrystal surfaces are relatively weak. The introduction of a coordinating function group into Tween® compounds, through one of their OH-groups, overcomes the insufficient hydrophobic interaction, leading to high stability of the nanoparticle dual-interaction ligands. Therefore, the resulting Tween® derivatives (TDs) act as dual-interacting ligands having affinity for the surface of hydrophobic nanocrystals through both coordinate bonding and hydrophobic van der Waals interactions as shown in FIG. 4. The displacement of the hydrophobic ligand of the hydrophobic nanoparticle can be enhanced by the hydrophobic interaction, which can effectively concentrate the coordination complex forming portion of the dual-interaction ligand, promoting the displacement of the hydrophobic ligand of the hydrophobic particle. Conversely, the coordination of the dual-interaction ligand to the nanoparticle surface enhances the van der Waal bonding between a surface bound hydrophobic group and a dual-interaction ligand, as both are bound to the nanoparticle surface promoting their interaction over interaction with a hydrophobic group not otherwise attached to the nanoparticle surface.

As indicated above, two types of coordinating groups can be incorporated into the Tween® compound for specific binding to different types of nanocrystals. For noble-metal particles and semiconductor QDs, a dithiol coordinating group is included into Tween® compounds, as illustrated in FIG. 3a) for the introduction of a dithiol group from lipoic acid. For nanocrystals of transition-metal oxides, such as $Fe_3O_4$, a coordination group with a diol functionality is included into the Tween® compound, as illustrated in FIG. 3b) for a diol containing dual-interaction ligand derived from dopamine.

In another embodiment of the invention, the dual-interaction ligands are functionalized for bonding to antibodies or other biomolecules to allow specific interactions or binding of a resulting nanoparticle-dual interaction ligand complex with a biomolecules. As illustrated in FIG. 3c), a carboxyl group for bonding of a protein or other biomolecules can be attached to the Tween® molecule in addition to the coordinating group, where the carboxylic acid derived from succinic anhydride is formed after the introduction of the dithiol complexing group. In this manner, these stable water soluble nanoparticles can be linked covalently to antibodies.

In another embodiment, a method of preparing a dual-interaction ligand involves the functionalization of a Tween® compound. The typical reaction yields for introducing a single complexing group to a Tween® compound is higher than 80%. The structures of these TDs were confirmed using $^1$H NMR and electron-spray-ionization mass spectrometry (ESI-MS) indicates that the majority of the product is the dual-interaction ligand with a single coordination group attached to the Tween® compound, but the specific positions of the attached functional groups in the TDs are not necessarily the position illustrated in FIG. 3. Embodiments of a dithiol and a diol dual-interaction ligand are illustrated below in the experimental section. In yet another embodiment of the method, a method to further functionalize the dual-interaction ligand by the attachment of an antibody or other biological molecule involves the incorporation of an acid functionality to another arm of the Tween® compound.

MATERIALS AND METHODS

Chemicals

Butylamine (99%), dimethylaminopyridine (DMAP, 99%), dopamine hydrochloride, hexamethyldisilathiane ($(TMS)_2S$), lipoic acid ≥99%), 1-methyl-2-pyrrolidinone (NPA, ≥ 99%), N,N'-diisopropyl carbodiimide (DIPC, 99%), iron chloride ($FeCl_3.6H_2O$, 98%), 1-octadecene (ODE, 90%), octadecylamine (ODA, 97%), oleic acid (OA, 90%), p-toluenesulfonic acid monohydrate (98%), rhodamine 6G (99%), tributylphosphine (TBP, 97%), trioctylphosphine oxide (TOPO, 99%), polyethylene glycol sorbitan monolaurate (Tween-20), polyethylene glycol sorbitan monolaurate (Tween-40), polyethylene glycol sorbitan monostearate (Tween-60) and polyethylene glycol sorbitan monooleate (Tween-80) were purchased. Cadmium oxide (CdO, 99.998%), selenium (Se, 99.99%), dodecyl trimethylammonium bromide (DTAB, 97%) were purchased. Sodium oleate (95%) was purchased. Nanopure water (18.2 MΩ·cm) was prepared by a Barnstead Nanopure Diamond system. All other solvents were purchased.

The reagent 4-(N,N'-Dimethylamino)pyridinium-4-toluenesulfonate (DPTS) was prepared by mixing THF solutions of DMAP (2 M, 50 mL) and p-toluenesulfonic acid monohydrate (2 M, 50 mL) at room temperature with stirring. The resulting precipitate was filtered and dried under vacuum.

Analytical Methods $^1$H-NMR measurements $^1$H-NMR spectra were recorded using a Varian Mercury NMR Spectrometer (300 MHz). The samples were prepared by adding aliquots of products (10 mg) into a deuterated solvent ($CDCl_3$, ~0.6 mL).

Fluorescence Quantum Yields (QY) Determination

Fluorescent spectra were measured using a spectrofluorometer (Fluorolog-3, Horiba Jobin Yvon, Irvine, Calif.). Room-temperature fluorescence QY of the CdSe/ZnS core/shell QDs was determined by using a literature method. LD690 (63% QY) was used as reference and excitation wavelength was 500 nm.

Dynamic Light Scattering

The nanoparticle aqueous solutions were filtered through a 0.22-μm MCE syringe filter (Fisher Scientific) first. The hydrodynamic sizes of nanocrystals were obtained from a dynamic light scattering (DLS) (Brookhaven Instruments Corporation, Holtsville, NY) at 25° C.

TEM Measurements

TEM measurements were performed on a JEOL 200CX operated at 200 kV. The specimens were prepared as follows: a particle solution (10 μL) was dropped onto a 200-mesh copper grid, and dried overnight at ambient conditions.

Synthesis of Tween-derivatives (TDs)

TD20-a

To prepare [5-(1,2-Dithiolan-3-yl)-1-oxopentyl]polyethylene glycol sorbitan monolaurate (TD20-a), Tween-20 (4.91 g, 4.0 mmol), lipoic acid (0.83 g, 4.0 mmol), and DPTS (1.37 g, 4.4 mmol) were mixed in $CH_2Cl_2$ (20 mL) and stirred for several minutes at room temperature. Then, DIPC (0.63 mL, 4.4 mmol) was added to the mixture. After being stirred at room temperature overnight, the reaction mixture was washed with water (30 mL) four times. The organic phase was dried over magnesium sulfate ($MgSO_4$), filtered and concentrated. The crude product was purified by column chromatography on silica gel (eluents: ethyl acetate/hexane 9:1 and chloroform/methanol 9:10). Yield: 88%. $^1$H-NMR (300 MHz, $CDCl_3$): δ (ppm) 0.88 (t, 3H), 1.25 (m, 16H), 1.47 (m, 2H), 1.63 (m, 6H), 1.90 (m, 1H), 2.33 (m, 4H), 2.45 (m, 1H), 3.13 (m, 3H), 3.63 (m, 82H), 4.21 (m, 4H), 4.56 (m, 2H).

TD20-L

To prepare (6,8-Dimercapto-1-oxoocty)polyethylene glycol sorbitan monolaurate (TD20-L), TD20-a (4.96 g, 3.5 mmol) was dissolved in a mixture of EtOH/water (50 mL, 1:4). Then $NaBH_4$ (0.23 g, 6.0 mmol) was slowly added. The reaction mixture was stirred for 2 h until the solution became colorless. Then, the solution was diluted with water (50 mL) and extracted with $CHCl_3$ (50 mL) five times. The combined organic phase was dried over $MgSO_4$ and filtered. The solvent was removed under reduced pressure to give a white oily product. Yield: 82%. ESI-MS: m/z 1417.8 [M+H]$^+$. $^1$H-NMR (300 MHz, $CDCl_3$,): δ (ppm) 0.88 (t, 3H), 1.24 (m, 16H), 1.47 (m, 2H), 1.63 (m, 6H), 1.90 (m, 1H), 2.33 (m, 4H), 2.92 (m, 1H), 2.70 (m, 3H), 3.63 (m, 82H), 4.21 (m, 4H), 4.56 (m, 2H).

TD40-L

The synthesis of (6,8-Dimercapto-1-oxoocty)polyethylene glycol sorbitan monopalmitate (TD40-L) was carried out using similar conditions as those for the synthesis of TD20-L. ESI-MS: m/z 1473.8 [M+H]$^+$. $^1$H-NMR (300 MHz, $CDCl_3$,): δ(ppm) 0.88 (t, 3H), 1.24 (m, 24H), 1.47 (m, 2H), 1.63 (m, 6H), 1.90 (m, 1H), 2.33 (m, 4H), 2.92 (m, 1H), 2.70 (m, 3H), 3.63 (m, 82H), 4.21 (m, 4H), 4.56 (m, 2H).

TD60-L

The synthesis of (6,8-Dimercapto-1-oxoocty)polyethylene glycol sorbitan monostearate (TD60-L) was carried out using similar conditions as those for the synthesis of TD20-L. ESI-MS: m/z 1501.9 [M+H]$^+$. $^1$H-NMR (300 MHz, $CDCl_3$,): δ (ppm) 0.88 (t, 3H), 1.24 (m, 28H), 1.47 (m, 2H), 1.63 (m, 6H), 1.90 (m, 1H), 2.33 (m, 4H), 2.92 (m, 1H), 2.70 (m, 3H), 3.63 (m, 82H), 4.21 (m, 4H), 4.56 (m, 2H).

TD80-L

The synthesis of (6,8-Dimercapto-1-oxoocty)polyethylene glycol sorbitan monooleate (TD80-L) was carried out using similar conditions as those for the synthesis of TD20-L ESI-MS: m/z 1499.9 [M+H]$^+$. $^1$H-NMR (300 MHz, CDCl3,): δ (ppm) 0.88 (t, 3H), 1.24 (m, 20H), 1.47 (m, 2H), 1.63 (m, 6H), 1.90 (m, 1H), 2.33 (m, 4H), 2.92 (m, 1H), 2.70 (m, 3H), 3.63 (m, 82H), 4.21 (m, 4H), 4.56 (m, 2H), 5.34 (t, 2H).

TD20-b

The synthesis of (3-Carboxy-1-oxopropyl)polyethylene glycol sorbitan monolaurate (TD20-b) was performed by mixing Tween-20 (4.91 g, 4.0 mmol), succinic anhydride (0.41 g, 4.0 mmol) and DMAP (18 mg, 0.15 mmol) in 20 ml of dry acetonitrile and refluxing the mixture overnight with stirring. After the solution was cooled to room temperature, the solvent was evaporated under reduced pressure. The resulting oily residue was dissolved in $CHCl_3$ (100 mL) and washed with HCl (1 N, 40 mL) three times and washed with water (60 mL) three times. The organic phase was dried over $MgSO_4$ and filtered. The yellow oily product was obtained after removal of the solvent. Yield: 93%. $^1$H-NMR (300 MHz, $CDCl_3$): δ (ppm) 0.88 (t, 3H), 1.25 (m, 16H), 1.60 (m, 2H), 2.32 (t, 2H), 2.63 (s, 4H), 3.63 (m, 82H), 4.23 (m, 4H), 4.57 (m, 2H).

TD 20-c

The preparation of [4-[(2,5-Dioxo-1-pyrrolidinyl)oxy]-1,4-dioxobutyl]polyethylene glycol sorbitan monolaurate (TD20-c) commenced with the mixing of TD20-b (4.85 g, 3.7 mmol) and N-hydroxysuccinimide (NHS, 0.43 g, 3.7 mmol) in $CH_2Cl_2$ (20 mL) followed by the addition of EDC (0.71 g, 3.7 mmol). After stirring at room temperature overnight, the reaction mixture was diluted with $CH_2Cl_2$ (30 mL) followed by washing with HCl (0.1 N, 60 mL) twice and then brine (60 mL) twice. The organic phase was dried over $MgSO_4$, filtered and concentrated. The crude product was purified by column chromatography on silica gel (eluents: ethyl acetate/hexane 9:1) and chloroform/methanol 9:1) to give a yellow oily product. Yield: 89%. $^1$H-NMR (300 MHz, $CDCl_3$): δ (ppm) 0.88 (t, 3H), 1.25 (m, 16H), 1.60 (m, 2H), 2.32 (t, 2H), 2.84 (s, 4H), 2.78(t, 2H), 2.97 (t, 2H), 3.63 (m, 82H), 4.26 (m, 4H), 4.57 (m, 2H).

TD20-D

The preparation of [[[2-(3,4-Dyhydroxyphenyl)ethyl]amino]carbonyl]polyethylene glycol sorbitan monolaurate (TD20-D) commenced with the mixing of dopamine hydrochloride (0.63 g, 3.3 mmol) and triethylamine (0.33 g, 3.3 mmol) in 1 ml of pyridine. The mixture was added to a solution of TD20-c (4.63 g, 3.3 mmol) in pyridine (10 mL). After stirring for 2 h, the pyridine and solvent were removed under reduced pressure. The oily residue was dissolved in $CH_2Cl_2$ (20 mL) and the insoluble solid was filtered away. Then, the solution was washed with water (30 mL) three times. The organic phase was dried over $MgSO_4$ and filtered. A dark yellow oily product was obtained after evaporation of the solvent. Yield: 90%. ESI-MS: m/z 1463.9 [M+H]$^+$. $^1$H-NMR (300 MHz, $CDCl_3$,): δ (ppm) 0.88 (t, 3H), δ$_b$ 1.25 (m, 16H), 1.62 (m, 2H), 2.33 (m, 2H), 2.43 (t, 2H), 2.84 (m, 4H), 3.435 (t, 2H), 3.64 (m, 84H), 4.21 (m, 4H), 4.56 (m, 2H), 6.55 (d, 1H), 6.70 (s, 1H) and 6.79 (d, 1H).

TD40-D

The synthesis of [[[2-(3,4-Dyhydroxyphenyl)ethyl]amino]carbonyl]polyethylene glycol sorbitan monopalmitate (TD40-D) was performed using similar conditions to those for the synthesis of TD20-D. ESI-MS: m/z 1519.9 [M+H]$^+$. $^1$H-NMR (300 MHz, $CDCl_3$,): δ (ppm) 0.88 (t, 3H), 1.25 (m, 24H), 1.62 (m, 2H), 2.33 (m, 2H), 2.43 (t, 2H), 2.84 (m, 4H), 3.435 (t, 2H), 3.64 (m, 84H), 4.21 (m, 4H), 4.56 (m, 2H). 6.55 (d, 1H), 6.70 (s, 1H) and 6.79 (d, 1H).

TD60-D

The preparation of [[[2-(3,4-Dyhydroxyphenyl)ethyl]amino]carbonyl]polyethylene glycol sorbitan monolaurate (TD60-D) was carried out using similar conditions as those for the synthesis of TD20-D. ESI-MS: m/z 1547.9 [M+H]$^+$.

$^1$H-NMR (300 MHz, CDCl$_3$,): δ (ppm) 0.88 (t, 3H), 1.25 (m, 26H), (m, 2H), 2.33 (m, 2H), 2.43 (t, 2H), 2.84 (m, 4H), 3.435 (t, 2H), 3.64 (m, 84H), 4.21 (m, 4H), 4.56 (m, 2H), 6.55 (d, 1H), 6.70 (s, 1H) and 6.79 (d, 1H).

TD80-D

In like manner to TD60-D, [[[2-(3,4-Dyhydroxyphenyl) ethyl]amino]carbonyl]polyethylene glycol sorbitan monolaurate (TD8O-D) was prepared. ESI-MS: m/z 1545.9 [M+H]$^+$. $^1$H-NMR (300 MHz, CDCl$_3$,): δ (ppm) 0.88 (t, 3H), 1.25 (m, 20H), 1.62 (m, 2H), 1.99 (m, 4H), 2.33 (m, 2H), 2.43 (t, 2H), 2.84 (m, 4H), 3.435 (t, 2H), 3.64 (m, 84H), 4.21 (m, 4H), 4.56 (m, 2H), 5.34 (t, 2H), 6.55 (d, 1H), 6.70 (s, 1H) and 6.79 (d, 1H).

TD$_{20}$-e

The preparation of α-[5-(1,2-Dithiolan-3-yl)-1-oxopentyl]-ω-(3-carboxy-1-oxopropyl) poly-ethylene glycol sorbitan monolaurate (TD$_{20}$-e) was carried out by mixing TD20-a (4.96 g, 3.5 mmol), succinic anhydride (0.36 g, 3.5 mmol) and DMAP (18 mg, 0.15 mmol) in dry acetonitrile (20 mL) followed by refluxing overnight with stirring. The solution was cooled to room temperature and the solvent evaporated under reduced pressure. The oily residue was dissolved in CHCl$_3$ (10 mL) and washed with HCl solution (1 N, 40 mL) twice and with water (50 mL) twice. The organic phase was dried over MgSO$_4$ and filtered. The yellow oily product was obtained after evaporation of the solvent. Yield: 98%. $^1$H-NMR (300 MHz, CDCl$_3$,): δ (ppm) 0.88 (t, 3H), 1.24 (m, 16H), 1.46 (m, 2H), 1.63 (m, 6H), 1.90 (m, 1H), 2.32 (m, 4H), 2.45 (m, 1H), 2.65 (2.66, 4H), 3.13 (m, 3H), 3.63 (m, 82H), 4.21 (m, 6H), 4.56 (m, 2H).

TD$_{20}$-LC

The synthesis of α[5-(1,2-Dithiolan-3-yl)-1-oxopentyl]-ω-(6,8-dimercapto-1-oxoocty)-polyethylene glycol sorbitan monolaurate (TD$_{20}$-LC) by cooling a TD20-e (5.14 g, 3.4 mmol) in NaHCO$_3$ aqueous solution (0.25 M, 100 mL) in an ice bath for 5 minutes and then slowly adding NaBH$_4$ (0.53 g, 14 mmol). The reaction mixture was stirred for 2 h until the reaction mixture turned colorless. To quench the reaction HCl (6 N, 10 mL) was added. The resulting mixture was extracted with CHCl$_3$ (50 mL) five times. The combined organic solution was dried over MgSO$_4$ and filtered. A white oily product was obtained after evaporation of the solvent. Yield: 92%. ESI-MS: m/z 1517.9 [M+H]$^+$. $^1$H-NMR (300 MHz, CDCl$_3$,): δ (ppm) 0.88 (t, 3H), 1.24 (m, 16H), 1.47 (m, 2H), 1.63 (m, 6H), 1.90 (m, 1H), 2.33 (m, 4H), 2.92 (m, 1H), 2.65 (2.66, 4H), 2.70 (m, 3H), 3.63 (82H), 4.21 (m, 6H), 4.56 (m, 2H).

Hydrophobic Nanocrystal Synthesis

The synthesis of 1-dodecanethiol-capped 6.6-nm gold nanocrystals was carried out according to the literature procedure. In a typical synthesis, AuCl$_3$ (0.068 g) was dissolved in a DTAB solution (0.185 g of DTAB in 20 ml of toluene) with ultrasonication to form a dark orange solution. A freshly-prepared aqueous solution of NaBH$_4$ (75 μmol) was added dropwise to the solution with vigorous stirring. After 20 minutes, 1-dodecanethiol (1.6 mL) was added and the stirring was continued for 10 minutes. The nanoparticles were precipitated by adding ethanol, and the solid was re-dispersed in toluene (20 mL) in the presence of 1-dodecanethiol (1.6 mL) and refluxed for 30 minutes under nitrogen. The nanocrystals were precipitated from the reaction solution with ethanol (30 mL), isolated by centrifugation and re-dispersed in CHCl$_3$. The resulting nanoparticles have a diameter of 6.6 nm with a standard deviation of 7.0%.

Oleic-acid-capped 5.8-nm Fe$_3$O$_4$ nanocrystals were synthesized according to the literature method.

Oleylamine-capped 5.6-nm CdSe/ZnS core/shell nanocrystals were prepared by a two-step procedure consisting of synthesis of CdSe core nanocrystal and growth of ZnS layers. The syntheses were conducted according to the literature method.

Synthesis of Water Soluble Nanoparticles

Figure 5:
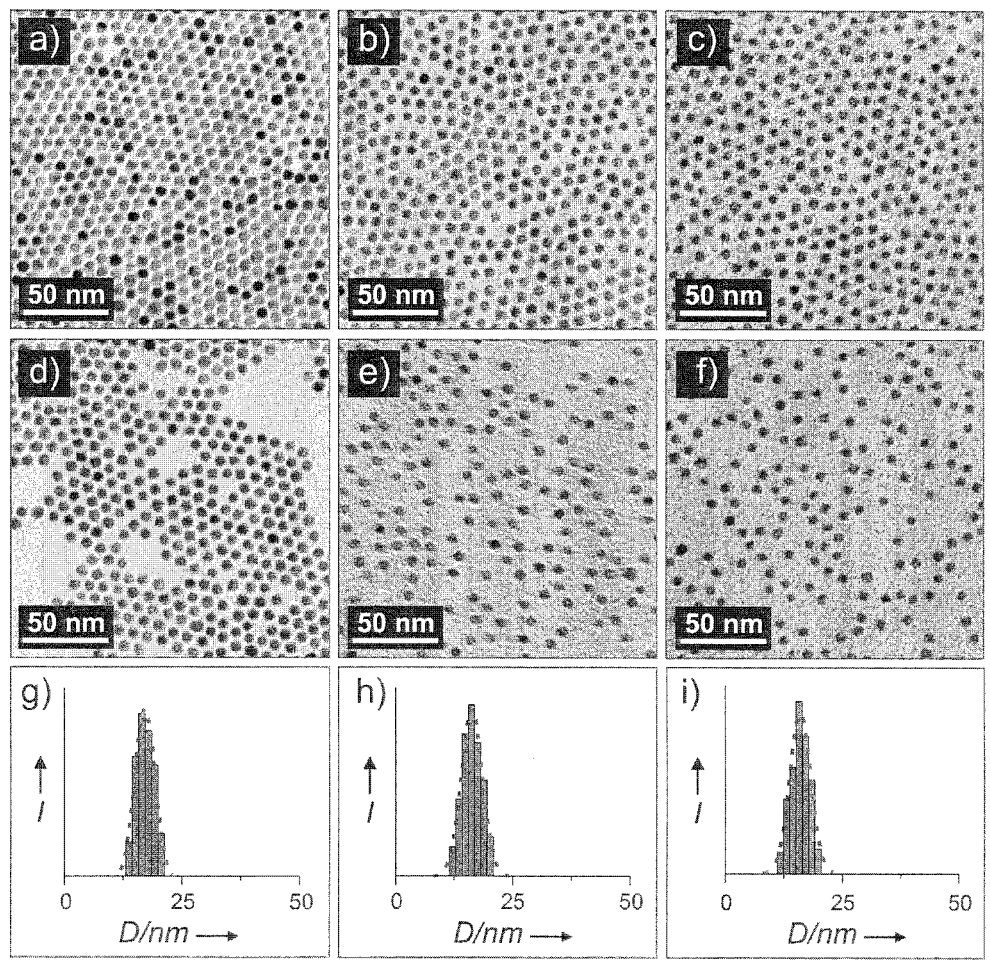
FIG. 5 shows reproductions of transmission electron microscope (TEM) images of hydrophobic a) 6.6 nm Au, b) 5.8 nm $Fe_3O_4$ and c) 5.6 nm CdSe/ZnS nanocrystals and the derived water soluble nanocrystals complexes according to embodiments of the invention with d) Au, e) $Fe_3O_4$ and f) CdSe/ZnS. Grafts of the dynamic light scattering (DLS) spectra of the water soluble nanocrystals are shown for g) Au, h) $Fe_3O_4$ and i) CdSe/ZnS.

To examine the function of these TD ligands, three types of hydrophobic nanocrystals are used: gold nanocrystals (6.6 nm in diameter with a standard deviation (σ) of 7%), Fe$_3$O$_4$ (5.8 nm in diameter with r of 6.0%), and CdSe/ZnS QDs (5.6 nm in diameter with σ of 8.0%) (FIG. 5a-c). In the first set of experiments, TD20-L (or TD20-D), as shown in FIG. 3, was used to functionalize the gold and CdSe/ZnS (or Fe3O4) nanocrystals, respectively. The ligand-exchange reactions were performed in chloroform for 20 min. After chloroform evaporation, the resulting hydrophilic nanocrystals are highly soluble in water, with a transfer yield of nearly 100%. The excess ligands in the hydrophilic-nanocrystal solutions were washed from the hydrophilic nanocrystals by a series of four spin-filtration and washings.

Hydrophobic nanoparticles (i.e., Au, Fe$_3$O$_4$ or CdSe/ZnS) (25 nmol) and TDs (e.g., TD$_N$-L, TD$_N$-D or TD$_{20}$-LC) (10 μmol) were mixed in CHCl$_3$ (5 mL). The solution was stirred at room temperature for 10 minutes. Then triethylamine (0.05 mL) was added into the mixture. The resulting mixture was stirred further for 10 minutes. After evaporation of the solvent, these nanocrystals were re-dispersed in water. The nanocrystal solution was filtered through a 0.22 μm MCE syringe filter (Fisher Scientific). The excess of TD ligands was removed by repeating four times the redispersions in water and spin filtrations (Millipore, 10K NMWL, 10000×g, 10 min). The resulting nanocrystals were re-dispersed in water (pH 7) for further studies.

Figure 6A:
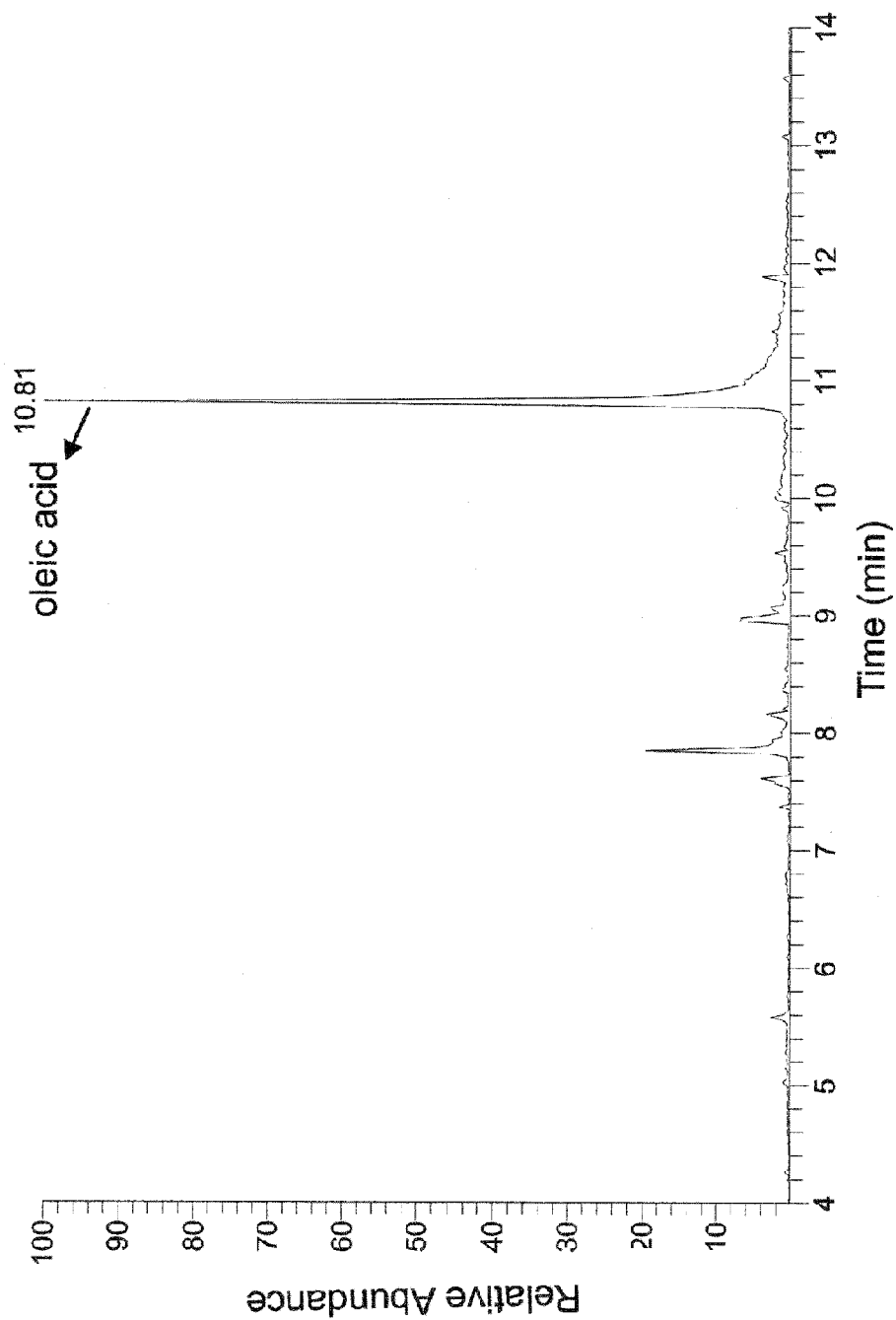
FIG. 6 shows gas-chromatography mass spectra of the ligands attached to TD20-D-functionalized $Fe_3O_4$ nanocrystals, a) gas-chromatograph; and b) mass spectrum of the compound with a retention time of 10.81 min. in the gas gas-chromatograph.
Figure 6B:
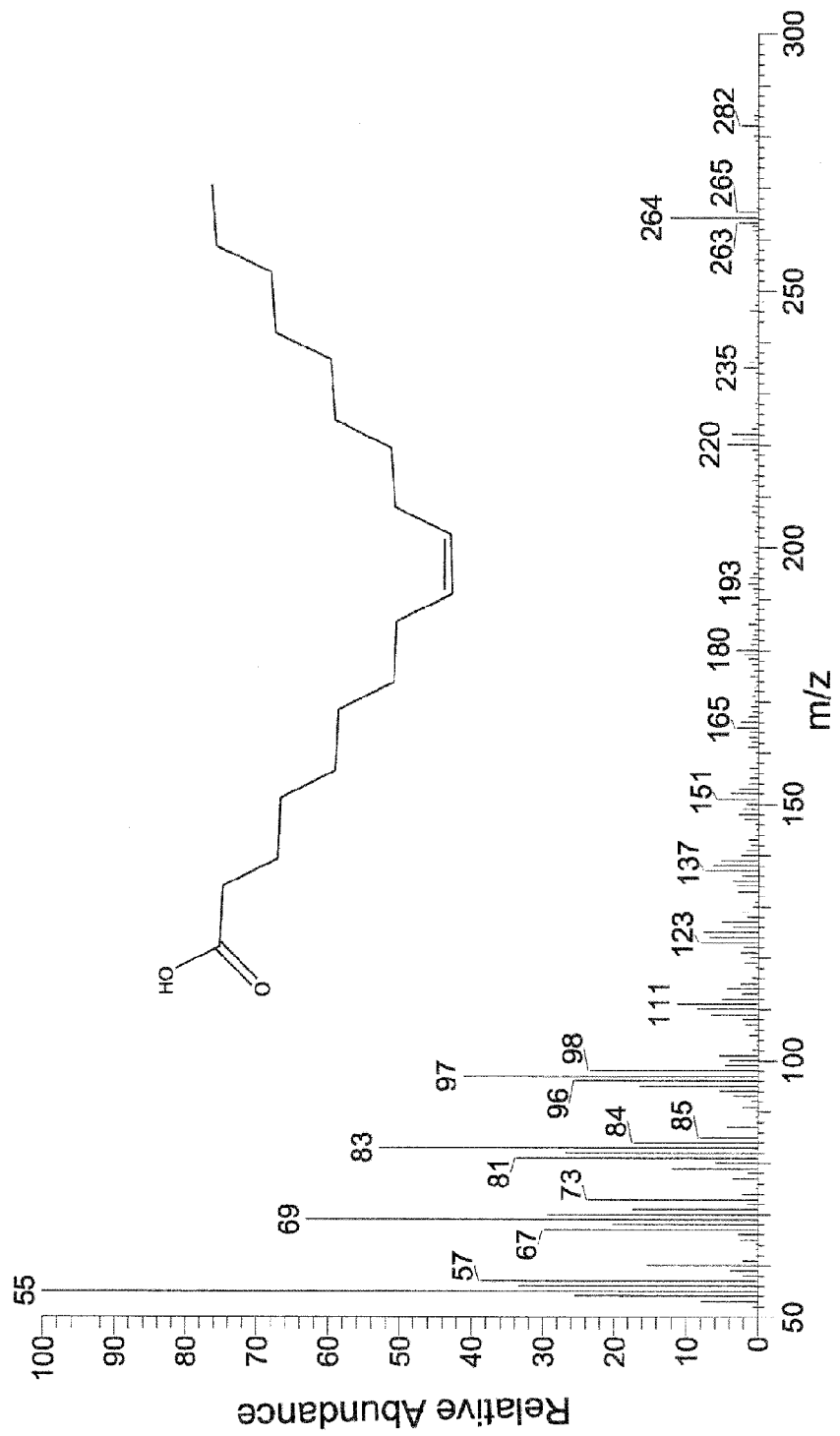

TEM measurements show that the TD-functionalized hydrophilic nanocrystals exhibit nearly identical size and shape, as compared to their hydrophobic counterparts (FIG. 5d-f). Dynamic light scattering (DLS) measurements show that the HDs of these nanocrystals are 17.1 nm for the TD20-L-functionalized Au particles, 16.3 nm for the TD20-D-functionalized Fe3O4 nanocrystals, and 15.9 nm for the TD20-L-functionalized CdSe/ZnSe QDs (FIG. 5g-i). By subtracting the HDs from their respective core sizes, nearly identical shell thickness of about 5.2 nm are obtained for all three types of nanocrystals. The measured shell thickness is nearly identical to the average length of these TD ligands (~4.9 nm). This result indicates that only one monolayer of TD ligands is attached to the nanocrystal surface. In addition, GC-MS measurements show that these TD ligands do not entirely remove the original hydrophobic ligands of the nanocrystals. In a sample of TD20-D-functionalized Fe$_3$O$_4$ nanocrystals, oleic acid ligands from the hydrophobic nanoparticle were unambiguously identified by GC-MS as shown in FIG. 6. These results indicate that TD ligands indeed functionalize hydrophobic nanocrystals through coordinate bonding as well as the hydrophobic van der Waals interactions between the fatty-acid chain in the TD ligands and the hydrophobic ligands on the nanocrystals as shown in FIG. 4. This nanocrystal functionalization with dual-interaction ligands is also supported by the results of stability studies disclosed below.

Stability of Water Soluble Nanoparticles

Stability Testing

Figure 7:
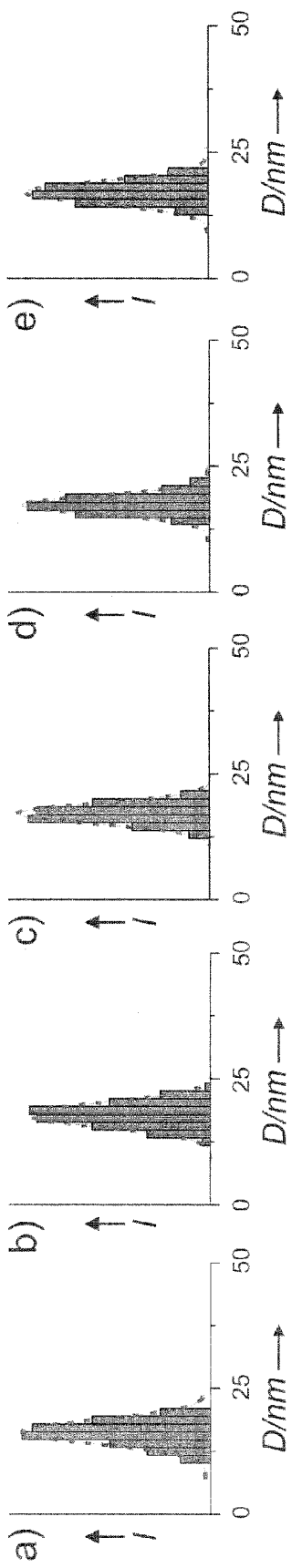
FIG. 7 shows DLS spectra for five dual-interaction ligand nanoparticles, according to an embodiment of the invention, used for parallel stability-test experiments where the nanocrystal hydrodynamic size a) 16.3 nm, b) 17.8 nm, c) 17.1 nm, d) 17.3 nm, and e) 17.0 nm.

Each stability test was repeated more than five times using the same batch of TD-capped nanocrystals. The sample standard deviation (S) and relative standard deviation (σ) were calculated by the following equations, respectively:

$$S = \sqrt{\frac{1}{N-1}\sum_{i=1}^{N}(x_i - \bar{x})^2} \text{ ; and } \sigma = S/\bar{x}$$

where $x_i$ is the data of each experiment and $\bar{x}$ is the average value of these experiments. For example, five sets of DLS data, as shown in FIG. 7, were obtained from five parallel stability-test experiments. The nanocrystal hydrodynamic size in each experiment is (a) 16.3 nm, (b) 17.8 nm, (c) 17.1 nm (d) 17.3 nm and (e) 17.0 nm leading to an average size of these five experiments of 17.1 nm±0.54 nm and σ=3.2%, as calculated by the above equations.

Figure 8:
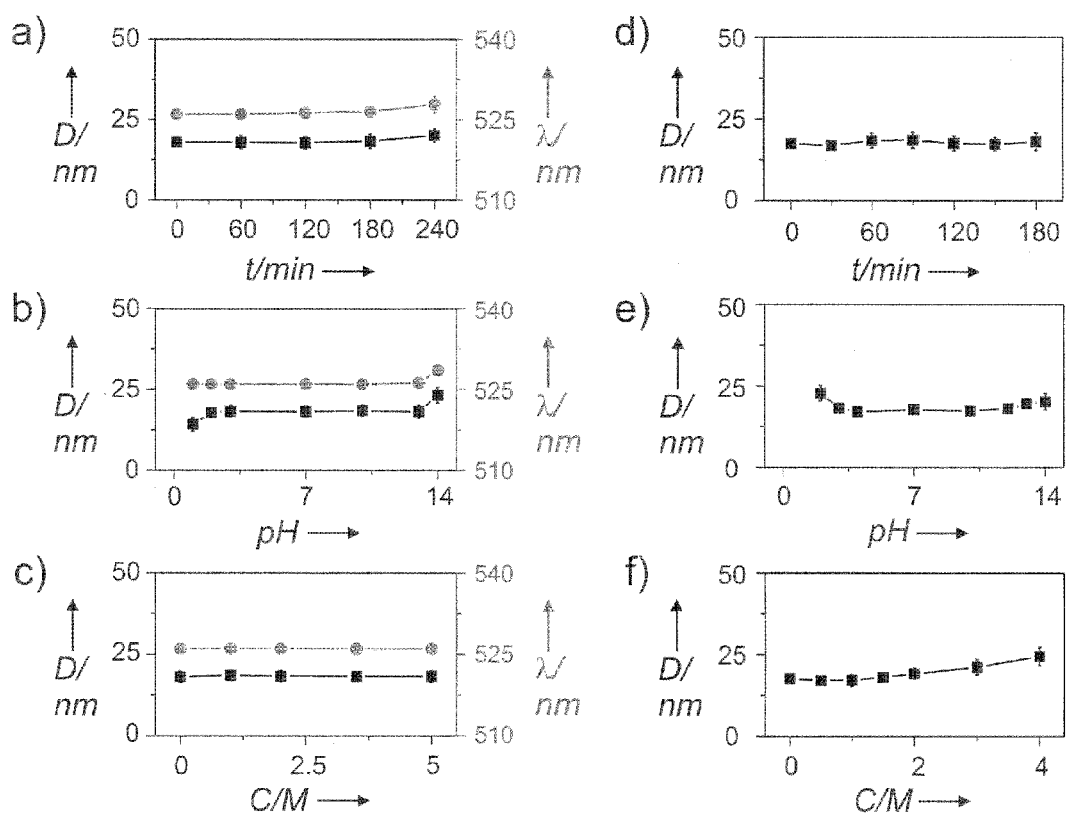
FIG. 8 shows plots of stability test results for TD20-L-functionalized 6.6 nm Au nanocrystals a) through c) and TD20-D-functionalized 5.8 nm $Fe_3O_4$ nanocrystals d) through f), where a) and d) indicates thermal stability at 100° C., b) and e) indicates pH stability, and c) and f) indicate salt stability as a function of NaCl concentration, and where squares indicate values determined by DLS and circles indicate values determined by UV-Vis spectra.

The stability of the hydrophilic nanocrystals was examined as a function of pH, salt concentration and the time for a thermal treatment at 100° C., as shown in FIG. 8. For the TD20-L-functionalized gold nanocrystals, the stability tests were monitored using both LDS and UV-Vis absorption spectroscopy. In boiling water (pH 6.5) for 4 h, these gold nanocrystals do not exhibit significant change in their HD, as measured using LDS, or in the position of their absorption peak, as measured by absorption spectroscopy (FIG. 8a). The results from pH-stability tests show that these hydrophilic gold nanocrystals are stable from pH 2 to 13 for more than one week. At pH 1, the HD of these particles is slightly decreased, but without a change in the position of absorption peaks for more than two hours. At pH 14, the particles show small changes in both HD and absorption-peak position, but the nanocrystal solution is stable for more than three days at this condition (FIG. 8b). In addition, the gold nanocrystals are stable in NaCl solutions with concentrations up to 5 M (FIG. 8c). These results show that TD20-L-functionalized gold nanocrystals exhibit extraordinary stability in various extreme conditions and this stability is even higher than that of gold nanocrystals heavily functionalized with alkylthiol-capped oligonucleotides, which have been used in commercial biomedical diagnosis due to their high stability in high-concentration salt solutions.

TD20-D-functionalized $Fe_3O_4$ nanocrystals also exhibit excellent stability in these tests. These $Fe_3O_4$ nanocrystals are stable in a solution of boiling water (pH 6.5) for 3 h (FIG. 8d). A series of pH-stability tests show that these $Fe_3O_4$ nanocrystals are stable from pH 3 to 14 for more than one week. At pH 2, the HD of these $Fe_3O_4$ nanocrystals slightly increases (FIG. 8e). Surprisingly, TEM measurements show that after a 2-h treatment at pH 2 the nanocrystals exhibit no measurable change in size and shape, as compared with the nanocrystals in the control experiment at pH 7, as shown in FIG. 8. Moreover, these TD20-D-modified $Fe_3O_4$ nanocrystals are stable nearly instantly in a NaCl solution with concentrations up to 2 M. In a 4-M NaCl solution, these $Fe_3O_4$ nanocrystals are stable for more than 4 h (FIG. 8f). These results show that TD20-D-functionalized $Fe_3O_4$ nanocrystals exhibit a much higher stability than those $Fe_3O_4$ nanocrystals functionalized with PEGylated-dopamine ligands, which attach onto the nanocrystal surface through only coordinate bonding. Therefore, the excellent stability of TD-functionalized hydrophilic nanocrystals can be attributed to the ability of the TD ligands to attach onto the nanocrystal surface through both coordinate bonding and hydrophobic interactions.

Figure 9:
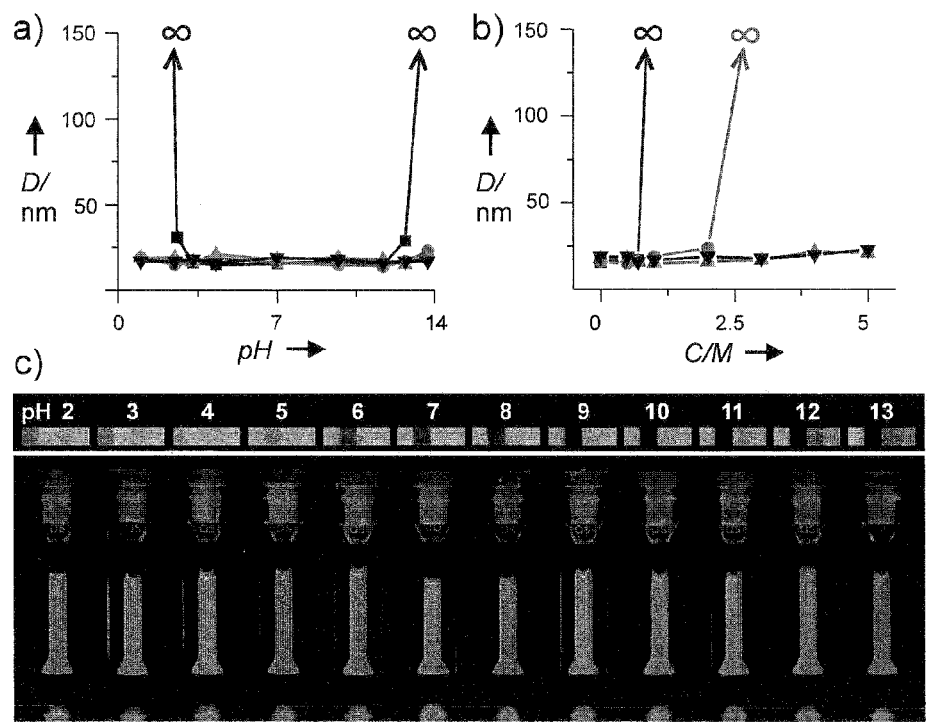
FIG. 9 shows plots of a) pH and b) NaCl stability as a function of fatty-acid chain length for TDN-L-functionalized 5.6 nm CdSe/ZnS nanocrystals where ■ represents TD20-L, ● represents TD40-L, ▲ represents TD60-L, and ▼ represents TD80-L functionalized nanocrystals, and c) is a reproduction of a fluorescence images of $TD_{80}$-L-functionalized 5.6-nm CdSe/ZnS nanocrystals as a function of pH.

To further explore the effect of the hydrophobic van der Waals interactions between TD ligands and the nanocrystal hydrophobic coating, the stability of TDN-L-functionalized CdSe/ZnS QDs was examined as a function of the fatty-acid chain in TDN-L ligands (N=20, 40, 60, or 80). In these experiments, 5.6nm-oleylamine-coated CdSe/ZnS particles were transferred into the aqueous phase through surface functionalization with the four types of TDN-L ligands. The resulting TD20-L-modified CdSe/ZnS nanocrystals are stable from pH 3.5 to 11 (FIG. 9a). Again this stability is higher than that of CdSe/ZnS particles functionalized with PEGylated-lipoic-acid ligands, which lack hydrophobic interactions with the nanocrystal surface. When the length of the fatty-acid chain was increased to C14 and C18, TDN-L-modified CdSe/ZnS nanocrystals (N=40, 60, or 80) are stable in the pH range, of 1 to 14, according to DLS measurements (FIG. 9a). Such fatty-acid-chain-dependent stability is also observed in the stability test results using NaCl solutions. TD20-L-modified particles are only stable in NaCl solutions up to 0.6 M, while TD40-L-modified particles are stable in a 2-M NaCl solution. With a further increase of fatty-acid length to C18, TD80-L- (or TD60-L)-functionalized CdSe/ZnS nanocrystals are stable in a nearly saturated NaCl solution (FIG. 9b). FIG. 9c shows the equivalence of the fluorescence intensity over a pH range of 2 through 13 for the TD80-L-functionalized CdSe/ZnS nanocrystals.

This chain-length-dependent stability suggests that the van der Waals interactions between the fatty-acid chains and the oleylamine coating play a significant role in stabilizing nanocrystals by the dual-interaction ligands in aqueous solutions. The longer the fatty-acid chain, the greater the van der Waals interact with the oleylamine coating and other bound TD ligands. In addition, the van der Waals interactions create a hydrophobic shell on the nanocrystal surface. Such a hydrophobic shell can provide additional protection for the hydrophilic nanocrystals because this shell can prevent hydrophilic reagents (such as H+) from reacting with the nanocrystal surface. Indeed, it was found that the fluorescence quantum yield of TD80-L-functionalized CdSe/ZnS QDs is maintained at about 50% for one week in aqueous solutions between pH 4 and 12. Furthermore, the fluorescence brightness of these nanocrystals does not change significantly for 2 hours in an aqueous solution of pH 2.

Demonstration of Diagnostic Suitability
Antibody-Functionalized CdSe/Zns Nanocrystal QDs Hydrophilic CdSe/ZnS QDs with a diameter of 5.6 nm (δ~8.0%) and capped with a mixture of compound $TD_{20}$-L and $TD_{20}$-LC (5:1 molar ratio) were prepared as described above. CdSe/ZnS QDs (0.20 nmol) were dissolved in 2-(N-morpholino)ethanesulfonic-acid buffer solution (MES buffer, 0.1 M, 150 μL, pH=6.0). An aqueous solution of 1-ethyl-3-(3-dimethylaminipropopyl) carbodiimide (EDC, 5.0 mg/mL, 50 μL) and an aqueous solution of N-hydroxysulfosuccinimide (Sulfo-NHS, 5.0 mg/mL, 50 μL) were added to the QDs buffer solution. The mixture solution was incubated for 1 h at room temperature with gentle shaking. 2-mercaptoethanol (1.0 μL) was added to the reaction mixture to quench the EDC. Then the excess reducing agent and inactivated cross-linker were removed by filtering through a NAP-5 column. Phosphate Buffered Saline (PBS buffer, pH=7.4) was used as the elution buffer. The collected QD solution was concentrated to 50 μL by spin filter (10K NMWL, Millipore, 10000×g, 10 min) and re-dissolved in a PBS buffer solution (250 μL, pH 7.4). NS5A-specific mouse monoclonal antibody (100 μg) was added into the QD solution, and resulting mixture was incubated for 2 h at room temperature. Hydroxylamine (0.5 μL) was added to quench the reaction. The mixture was transferred to a spin filter (100K NMWL, Millipore, 10000×g, 10 min) and concentrated to 50 μL. A PBS buffer solution (200 μL, pH 7.4) was added and the mixture was spun again. The washing step was repeated 2 times to remove thoroughly the free antibodies. Finally, the purified antibody-functionalized QDs (0.15 mmol) were re-dispersed in a PBS buffer solution (450 μmL, pH 7.4). Sodium azide was added to the solution of antibody-functionalized QDs (with a concentration of 0.01% (w/v as a preservative).

Immunostaining Tests

Figure 10:
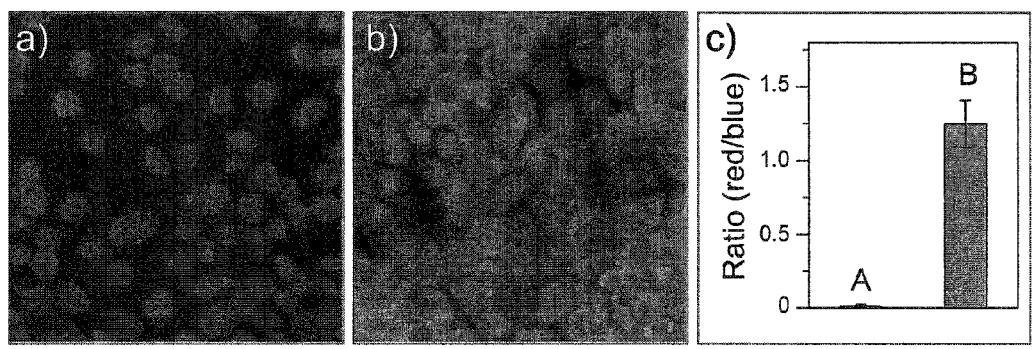
FIG. 10 shows reproductions of fluorescence microscope images of NS5A-containing FCA1 cells using TD-functionalized CdSe/ZnS core/shell nanocrystal QDs a) without, b) with NS5A-specific antibodies attached to the QDs, and c) the plot of the ratio of intensity of QDs labels in the FCA1 cells with the attached antibody is 75 times stronger than without.

To demonstrate the suitability of using these water-soluble nanocrystals for biomedical diagnosis, TD-modified CdSe/ZnS QDs were used as fluorescence labels to monitor the expression of a HCV (Hepatitis C virus) protein (NS5A) inside FCA1 cells. In these experiments, 5.6nm-oleylamine-capped CdSe/ZnS QDs were functionalized with a mixture of TD80-L and TD20-LC (5:1) and anti-HCV NS5A monoclonal antibodies were attached to the resulting QDs through an EDC coupling reaction. In a control test, the QDs without NS5A-specific antibodies showed very low non-specific absorption onto NS5A-containing FCA1-cell substrates (FIG. 10a). In contrast, the antibody-modified QDs exhibit a very high specific affinity to such substrates (FIG. 10b). Significantly, the fluorescence intensity from QDs labels is more than 75 times stronger than that in the control test (FIG. 10c). Details of the experimental procedure follow.

FCA1 HCV replicon cells were grown on glass coverslips for 24 h, and the cells were fixed in an ethanol solution with 5% acetic acid at −20° C. overnight. The fixed cells were washed with PBS (pH 7.4) at room temperature twice (5 minutes each time), and the cells were blocked by 1:50 normal goat serum for 30 min at room temperature. Then the cells were incubated with NS5A-specific-antibody functionalized QDs (50 nM, 0.20 mL) at room temperature for 1 h. After the cells were washed with PBS (pH 7.4) for 3 times (5 minutes each), the nuclei of the cells were counterstained with DAPI (4',6-diamidino-2-phenylindole, Vector Laboratories Inc, Burlingame, Calif.) as an internal reference, and the extra DAPI was washed away with PBS (pH 7.4). Finally, the FCA1 cells were examined under a fluorescence microscope (Olympus BX51, Olympus Imaging America Inc, Center Valley, Pa.). In the control test, TD-capped DQs (with the ratio of $TD_{80}$-L and $TD_{20}$-LC=5:1), which were not functionalized with NS5A-specific antibody, were used for staining FCA1 cells. Histograms of fluorescent images show the mean pixel intensities. The intensity ratio of blue channel (from DAPI) and red channel (from QDs) were calculated for each cell, and more than 300 cells were analyzed.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A dual-interaction ligand comprising:
   a hydrophilic base having a plurality of segments comprising polyethtlene glycol extending from a core of said hydrophilic base;
   at least one metal coordinating functionality; and
   at least one hydrophobic functionality, wherein said metal coordinating functionality is attached by a linking group to said hydrophilic base and said hydrophobic functionality is attached to said hydrophilic base.

2. The dual-interaction ligand of claim 1, wherein said hydrophilic base and said hydrophobic functionality comprises a polyethylene glycol (PEG) sorbitan fatty-acid esters (Tween), wherein said plurality of segments comprises four polyethylene glycol chains and said hydrophobic functionality comprises a fatty-acid ester.

3. The dual-interaction ligand of claim 2, wherein said Tween is Tween-20, Tween-40, Tween-60, or Tween-80.

4. The dual-interaction ligand of claim 1, wherein said metal coordinating functionality comprises a dithiol.

5. The dual-interaction ligand of claim 4, wherein said dithiol and said linking group are derived from dihydrolipoic acid.

6. The dual-interaction ligand of claim 1, wherein said metal coordinating functionality comprises a diol.

7. The dual-interaction ligand of claim 6, wherein said diol and said linking group are derived from a condensate of dopamine and succinic acid or succinic acid anhydride.

8. A method of preparing a water soluble or suspendable nanoparticle-dual-interaction ligand complex comprising:
   providing at least one hydrophobic nanoparticle containing a plurality of hydrophobic ligands;
   providing a plurality of dual-interaction ligands according to claim 1; and
   displacing at least some of said plurality of hydrophobic ligands with a plurality of dual-interaction ligands.

9. A water soluble or suspendable nanoparticle-dual-interaction ligand complex comprising:
   at least one nanoparticle; and
   a plurality of dual-interaction ligands comprising:
      a hydrophilic base having a plurality of segments comprising polyethylene glycol extending from a core of said hydrophilic base;
      at least one metal coordinating functionality; and
      at least one hydrophobic functionality, wherein said metal coordinating functionality is attached by a linking group to said base and said hydrophobic functionality is attached to said base.

10. The complex of claim 9, wherein said hydrophilic base and said hydrophobic functionality comprises a polyethylene glycol (PEG) sorbitan fatty-acid esters (Tween), wherein said plurality of segments of said hydrophilic base comprises four polyethylene glycol chains and said hydrophobic functionality comprises a fatty-acid ester.

11. The complex of claim 10, wherein said Tween is Tween-20, Tween-40, Tween-60, or Tween-80.

12. The complex of claim 9, wherein said metal coordinating functionality comprises a dithiol.

13. The complex of claim 12, wherein said dithiol and said linking group are derived from dihydrolipoic acid.

14. The complex of claim 9, wherein said metal coordinating functionality comprises a diol.

15. The complex of claim 14, wherein said diol and said linking group are derived from a condensate of dopamine and succinic acid or succinic acid anhydride.

16. The complex of claim 9, wherein said nanoparticle comprises a metal, metal oxide, or semiconductor nanocrystal.

17. The complex of claim 16, wherein said metal comprises Au, Ag, Ag/Au, Co, Pt, Pd, Cu or any combination thereof.

18. The complex of claim 16, wherein said metal oxide comprises $Fe_3O_4$, $Fe_2O_3$, $In_2O_3$, ZnO, $TiO_2$, $Gd_2O_3$, or any combination thereof.

19. The complex of claim 16, wherein said semiconductor comprises CdSe/ZnS, CdS/ZnS, CdS, CdSe, CdTe, InAs, InP, InP/ZnS, InAs/ZnSe, PbSe, PbS, PbTe or any combination thereof.

20. The complex of claim 9, further comprising a plurality of hydrophobic ligands.

21. The complex of claim 20, wherein said hydrophobic ligands comprise a C4-C30thiol, a C4-C30 fatty acid, a C4-C30 amine, a C4-C30 phosphine, a C4-C30dithiol, a C4-C30 diol, a C4-C30diamine, or any combination thereof.

22. The complex of claim 21, wherein said hydrophobic ligand comprises 1-dodecanethiol, oleic acid, or oleylamine.

23. The complex of claim 9, further comprising an antibody or other biomolecules attached by a linking group to a segment of at least one of said dual-interaction ligands.

24. A method for preparing a dual-interaction ligand comprising the steps of:
- providing a hydrophilic base having at least one hydrophilic segment comprising polyethylene glycol extending from a core of said hydrophilic base;
- attaching at least one hydrophobic functionality by a linking group to said hydrophilic base; and
- attaching at least one metal coordinating functionality by a linking group to said hydrophilic base.

25. The method of claim 24, wherein said hydrophilic base and said hydrophobic functionality comprises a polyethylene glycol (PEG) sorbitan fatty-acid esters (Tween), wherein said plurality of segments comprises four polyethylene glycol chains and said hydrophobic functionality comprises a fatty-acid ester.

26. The method of claim 25, wherein said Tween is Tween-20, Tween-40, Tween-60, or Tween-80.

27. The method of claim 24, wherein said metal coordinating functionality comprises a dithiol.

28. The method of claim 27, wherein said dithiol and said linking group are derived from dihydrolipoic acid.

29. The method of claim 24, wherein said metal coordinating functionality comprises a diol.

30. The method of claim 29, wherein said diol and said linking group are derived from a condensate of dopamine and succinic acid or succinic acid anhydride.

* * * * *

UNITED STATES PATENT AND TRADEMARK OFFICE
CERTIFICATE OF CORRECTION

PATENT NO. : 8,889,429 B2
APPLICATION NO. : 12/865056
DATED : November 18, 2014
INVENTOR(S) : Yunwei Charles Cao and Huimeng Wu Page 1 of 2

It is certified that error appears in the above-identified patent and that said Letters Patent is hereby corrected as shown below:

In the specification

Column 1,
Line 5, "APPLICATION" should read --APPLICATIONS--.

Column 3,
Line 44, "CdSc/ZnS" should read --CdSe/ZnS--.

Column 6,
Line 36, "acid ≥ 99%)" should read --acid (≥ 99%)--.

Column 9,
Line 32, "α[5-(1,2-Dithiolan" should read --α-[5-(1,2-Dithiolan--.

Column 10,
Line 9, "with r of" should read --with σ of--.
Line 28, "0.22 μm" should read --0.22-μm--.

Column 12,
Line 38, "CdSe/Zns" should read --CdSe/ZnS--.
Line 67, "(450 μmL" should read --(450 μL--.

In the claims

Column 14,
Line 35, "fatty-acid esters" should read --fatty-acid ester--.
Line 65, "C4-C30thiol" should read --C4-C30 thiol--.
Line 66, "C4-C30dithiol" should read --C4-C30 dithiol--.
Line 67, "C4-C30diamine" should read --C4-C30 diamine--.

Signed and Sealed this
Ninth Day of February, 2016

Michelle K. Lee
*Director of the United States Patent and Trademark Office*

CERTIFICATE OF CORRECTION (continued)
U.S. Pat. No. 8,889,429 B2

In the claims

<u>Column 15,</u>
Line 17, "fatty-acid esters" should read --fatty-acid ester--.